United States Patent
Ross et al.

(10) Patent No.: US 6,258,111 B1
(45) Date of Patent: Jul. 10, 2001

(54) APPARATUS AND METHOD FOR PERFORMING OPHTHALMIC PROCEDURES

(75) Inventors: Rod Ross, Laguna Niguel; Greggory Hughes, Fountain Valley; James C. Boore, Poway; Thomas E. Reimer, Anaheim, all of CA (US)

(73) Assignee: Scieran Technologies, Inc., Laguna Hills, CA (US)

( * ) Notice: Subject to any disclaimer, the term of this patent is extended or adjusted under 35 U.S.C. 154(b) by 0 days.

(21) Appl. No.: 09/369,406

(22) Filed: Aug. 5, 1999

Related U.S. Application Data

(63) Continuation-in-part of application No. 08/943,485, filed on Oct. 3, 1997.

(51) Int. Cl.$^7$ .................................................. A61B 17/32
(52) U.S. Cl. ............................................................. 606/171
(58) Field of Search .................................... 606/171, 159, 606/170, 180; 604/22

(56) References Cited

U.S. PATENT DOCUMENTS

| | | |
|---|---|---|
| Re. 23,496 | 5/1952 | Seeler . |
| 1,841,968 | 1/1932 | Lowry . |
| 1,847,658 | 3/1932 | Lasker . |
| 2,070,281 | 2/1937 | Leggiadro . |
| 2,708,437 | 5/1955 | Hutchins . |

(List continued on next page.)

FOREIGN PATENT DOCUMENTS

| | | |
|---|---|---|
| 2547185 | 4/1977 | (DE) . |
| 25 47 185 | 4/1977 | (DE) . |
| 2 549 727 | 2/1985 | (FR) . |

OTHER PUBLICATIONS

Murayama et al. "A Portable Air Driving Unit for Blood Pumps," Japanese Journal of Artificial Organs, vol. 14, No. 3, pp. 1206–1209 (English Translation).

Schuderi, et al., French article entitled La Chirurgie de la Cartaracte Congenitale, pp. 174–185 (English Translation).

Hayashi et al., Japanese Experience With Ventricular Assist Devices IBEE Engineering in Medicine and Biology Magazine Mar. 1986, pp. 30–36.

(List continued on next page.)

*Primary Examiner*—Michael Buiz
*Assistant Examiner*—Vikki Trinh
(74) *Attorney, Agent, or Firm*—Irell & Manella LLP

(57) ABSTRACT

A surgical cutting system. The cutting system includes a cutter which has an inner sleeve that moves adjacent to an aspiration port of an outer sleeve. The inner sleeve is coupled to a source of vacuum that pulls tissue into the outer port when the inner sleeve is moved away from the port. The inner sleeve then moves across the outer port and severs the tissue in a guillotine fashion. The tip of the inner sleeve may exert a spring force that assist in the cutting action of the cutter. The cutter includes a motor which creates an oscillating translational movement of the sleeve. The motor can be controlled by a controller that is coupled a foot pedal. The foot pedal and controller can be configured so that the motor decreases speed as the pedal is depressed by the operator. The inner sleeve is coupled to an aspiration line that pulls the severed tissue out of the cutter. The level of the aspiration vacuum pressure can be controlled by a variable regulator valve. The regulator valve is coupled to the controller and the foot pedal. The foot pedal may have a switch that allows the system to operate in either a variable speed mode or a variable pressure mode. In the variable speed mode the actuation of the foot pedal changes the speed of the motor. In the variable pressure mode the actuation of the foot pedal changes the vacuum level within the aspiration line.

4 Claims, 13 Drawing Sheets

U.S. PATENT DOCUMENTS

| | | |
|---|---|---|
| 2,824,455 | 2/1958 | Ristow et al. . |
| 3,033,196 | 5/1962 | Hay . |
| 3,252,623 | 5/1966 | Corbin et al. . |
| 3,266,494 | 8/1966 | Brownrigg . |
| 3,308,828 | 3/1967 | Pippin . |
| 3,399,677 | 9/1968 | Gould et al. . |
| 3,561,429 | 2/1971 | Jewett et al. . |
| 3,624,821 | 11/1971 | Henderson . |
| 3,693,613 | 9/1972 | Kelman . |
| 3,752,161 | 8/1973 | Bent . |
| 3,763,862 | 10/1973 | Spieth . |
| 3,815,604 | 6/1974 | O'Malley et al. . |
| 3,842,839 | 10/1974 | Malis et al. . |
| 3,884,238 | 5/1975 | O'Malley et al. . |
| 3,899,829 | 8/1975 | Storm et al. . |
| 3,903,881 | 9/1975 | Weigl . |
| 3,913,584 | 10/1975 | Walchle et al. . |
| 3,920,014 | 11/1975 | Banko . |
| 3,930,505 | 1/1976 | Wallach . |
| 3,977,425 | 8/1976 | Hayashida . |
| 3,982,539 | 9/1976 | Muriot . |
| 3,986,512 | 10/1976 | Walliser . |
| 4,004,590 | 1/1977 | Muriot . |
| 4,011,869 | 3/1977 | Seiler, Jr. . |
| 4,108,182 | 8/1978 | Hartman et al. . |
| 4,135,515 | 1/1979 | Muriot . |
| 4,137,920 | 2/1979 | Bonnet . |
| 4,168,707 | 9/1979 | Douvas et al. . |
| 4,178,707 | 12/1979 | Littlefield . |
| 4,204,328 | 5/1980 | Kutner . |
| 4,210,146 | 7/1980 | Banko . |
| 4,217,993 | 8/1980 | Jess et al. . |
| 4,223,676 | 9/1980 | Wuchinich et al. . |
| 4,245,815 | 1/1981 | Willis . |
| 4,246,902 | 1/1981 | Martinez . |
| 4,274,411 | 6/1981 | Dotson, Jr. . |
| 4,308,385 | 12/1981 | Goorden . |
| 4,308,835 | 1/1982 | Abbey . |
| 4,314,560 | 2/1982 | Helfgott et al. . |
| 4,320,761 | 3/1982 | Haddad . |
| 4,354,838 | 10/1982 | Hoyer et al. . |
| 4,395,258 | 7/1983 | Wang et al. . |
| 4,396,386 | 8/1983 | Kurtz et al. . |
| 4,428,748 | 1/1984 | Peyman et al. . |
| 4,445,517 | 5/1984 | Feild . |
| 4,474,411 | 10/1984 | Peters et al. . |
| 4,475,904 | 10/1984 | Wang . |
| 4,493,695 | 1/1985 | Cook . |
| 4,493,698 | 1/1985 | Wang et al. . |
| 4,522,371 | 6/1985 | Fox et al. . |
| 4,524,948 | 6/1985 | Hall . |
| 4,530,357 | 7/1985 | Pawloski et al. . |
| 4,540,406 | 9/1985 | Miles . |
| 4,555,645 | 11/1985 | Atkinson . |
| 4,589,414 | 5/1986 | Yoshida et al. . |
| 4,598,729 | 7/1986 | Naito et al. . |
| 4,706,687 | 11/1987 | Rogers . |
| 4,723,545 | 2/1988 | Nixon et al. . |
| 4,757,814 | 7/1988 | Wang et al. . |
| 4,768,506 | 9/1988 | Parker et al. . |
| 4,770,654 | 9/1988 | Rogers et al. . |
| 4,819,635 | 4/1989 | Shapiro . |
| 4,838,281 | 6/1989 | Rogers et al. . |
| 4,943,289 | 7/1990 | Goode et al. . |
| 4,988,347 | 1/1991 | Goode et al. . |
| 5,011,482 | 4/1991 | Goode et al. . |
| 5,013,310 | 5/1991 | Goode et al. . |
| 5,059,204 | 10/1991 | Lawson et al. . |
| 5,106,364 | 4/1992 | Hayafuji et al. . |
| 5,201,749 | 4/1993 | Sachse et al. . |
| 5,207,683 | 5/1993 | Goode et al. . |
| 5,226,910 | 7/1993 | Kajiyama et al. . |
| 5,273,524 | 12/1993 | Fox et al. . |
| 5,285,795 | 2/1994 | Ryan et al. . |
| 5,322,505 | 6/1994 | Krause et al. . |
| 5,354,268 | 10/1994 | Peterson et al. . |
| 5,364,395 | 11/1994 | West, Jr. . |
| 5,380,280 | 1/1995 | Peterson . |
| 5,403,276 | 4/1995 | Schechter et al. . |
| 5,476,473 | 12/1995 | Heckele . |
| 5,507,751 | 4/1996 | Goode et al. . |
| 5,520,684 | 5/1996 | Imran . |
| 5,527,332 | 6/1996 | Clement . |
| 5,531,744 | 7/1996 | Nardella et al. . |
| 5,643,304 | * 7/1997 | Schechter et al. .................. 606/171 |
| 5,700,240 | 12/1997 | Barwick, Jr. et al. . |
| 5,782,849 | 7/1998 | Miller . |

OTHER PUBLICATIONS

Scuderi, Par G., et al., "La Chirurgie De La Cataracte Congenitale", pp. 174–185.

Grieshaber & Company, Sutherland Rotatable Intraocular Microscissors Brochure.

JCERS and Tissue Removal Systems, Diskecter System Rapid Tissue Removal System Product Brochure.

Storz Instrument Company, MicroVit Vitrectomy System Instruction Manual.

Storz Instrument Company, MicroVit Vitrectomy System Product Brochure.

Storz Instrument Copmany, Irrigation Aspiration System Product Brochure.

United Surgical Corporation, Phacotron Plus Product Brochure.

Surgical Design Corporation, The Ultrasonic I/E Mini Probe Product Brochure.

Surgical Design Corporation, U.S. Phako System Product Brochure.

Coopervision Surgical, System VI Product Brochure.

Coopervision Surgical, Cavitron/Kelman Model 6500 E.I.S. and Model 7500 I/A System lil with AVIT Product Brochure.

Coopervision Surgical, Cavitron/Kelman Phaco–Emulsifier Aspirator Model 8001 Product Brochure.

Coopervision Surgical, Cavitron/Kelman Phaco–Emulsifier Aspirator Model 9001 Product Brochure.

Surgical Design Corporation, The Ocusystem Product Brochure.

Grieshaber & Company, MPC The Membrane Peeler Cutter Product Brochure.

Site Microsurgical Systems, Inc., Site TXR Product Catalog.

Parks, Marshall M., "Intracapsular Aspirator" pp. 59–74.

Crosby, Michael J., "V. On the Control of Artificial Hearts", pp. 89–114.

Mrava, Gene L., Advances in Biomedical Engineering and Medical Physics, vol. 3, Cardiac Engineering, Chapter III, Artificial Heart Driving Systems Historical Review and Future Possibilities, 1970, Interscience Publishers, pp. 31–68.

Van Oldenborgh, "Correction of late operative complications by means of a suction cutter", Trans. of Ophthal. Soc. of U.K., 1980, vol. 100, pp. 219–221.

Charles, Steve et al., "A Linear Suction Control for the Vitreous Cutter (Ocutome)", Arch. Ophthalmol., Sep. 1981, vol. 99, p. 1613.

Helfgott, Maxwell A., "A System for Variable Aspiration of Material Dissected from the Posterior Chamber", Ophthalmic Surgery, Jun. 1984, vol. 15, No. 6.

Murayama, T. et al., "A Portable Pneumatic Driving Unit for Blood Pumps", The Japanese Journal of Artificial Organs, 1985, vol. 14, No. 3, pp. 1206–1209.

Hayashi, Kozaburo et al., "Japanese Experience with Ventricular Assist Devices", IEEE Engineering in Medicine and Biology Magazine, Mar. 1986.

Grieshaber and Co. of Switzerland, Sutherland Rotatable Intraocular Microscissors, 2 pages.

JCERS and Tissue Removal Systems, Diskecter™ System, Rapid Tissue Removal System advertisement (1 page).

Micro–Vit Vitrectomy System Product Brochure and Instruction Manual.

Storz MicroVit Vitrectomy System, Today's Leading Opthalmic Surgeions are Demanding . . . (6 pages).

Storz Irrigation Aspiration System Product Brochure and Instruction Manual.

United Surgical Corporation Brochure on "Phacotron Plus," one page.

Surgical Design Company Brochure on Keates, Ultrasonic I/E Mini Probe by A. Banko, 2 pages.

Surgical Design Corporation Brochure on U.S. Phaco System, 1 page.

Coopervision Brochure on System VI, 1 page.

Coopervision Brochure on Cavitron/Kelman Model 6500 EIS and Model 7500, 6 pages.

Surgical Design Brochure on "The Ocusystem," 1 page.

Coopervision Brochure on Cavitron/Kelman Phaco–Emulsifier Aspirator Model 8001, 2 pages.

Coopervision Brochure on Cavitron/Kelman Phaco–Emulsifier Aspirator Model 9001, 6 pages.

Grieshaber of Switzerland Brochure on "MPC, The Membrane Peeler Cutter," 5 pages.

Brochure, Site TXR Systems, Site Microsurgical Systems, Inc. Horsham, Pennsylvania.

Parks, "Intracapsular Aspiration" article, pp. 59–74.

Van Oldenborgh, "Correction of Late Operative Complicatings by Means of a Suction Cutter," Ophthal. Soc. U.K. (1980), 110, 219, pp. 219–221.

Helfgott, "A System for Variable Aspiration of Material Dissected from the Posterior Chamber," Ophthalmic Surger, vol. 15, Jun. 1984, pp. 529–350.

Charles and Wang, "A Linear Suction Control for the Vitreous Cutter (Ocutome)," Arch. Ophthalmol. vol. 99, Sep. 1981, p. 1631.

Crosby, "On Control of Artificial Hearts," pp. 89–114.

Mrva, Cardiac Engineering, vol. 3, pp. 31–68.

\* cited by examiner

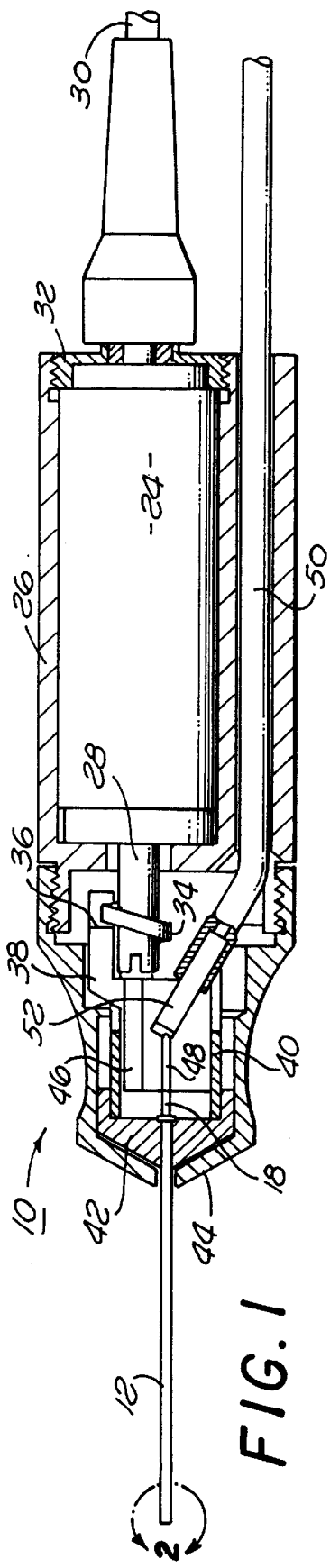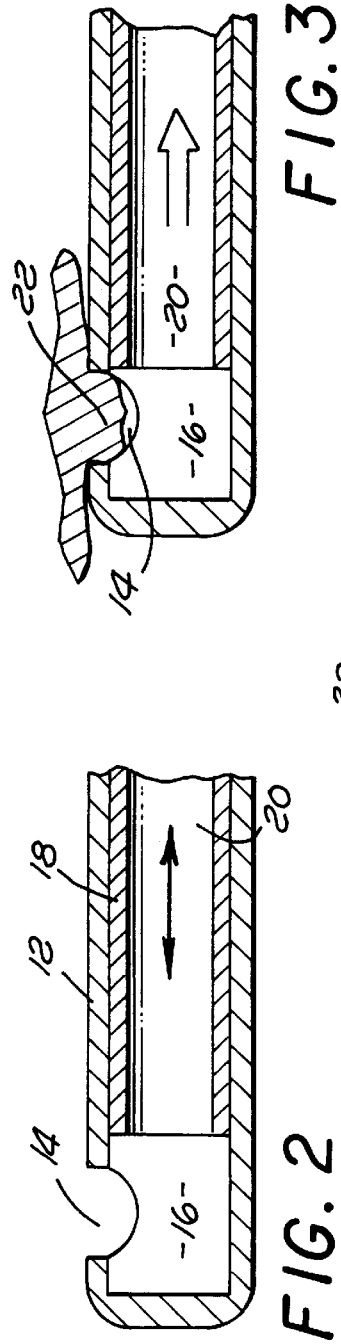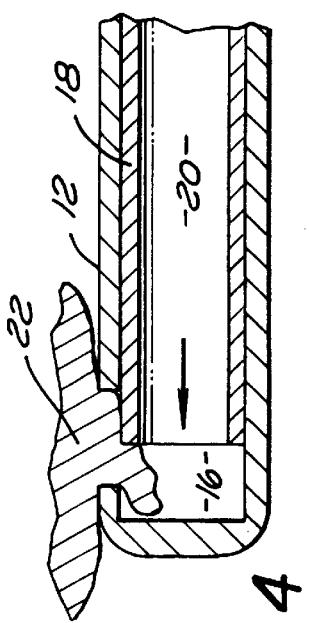

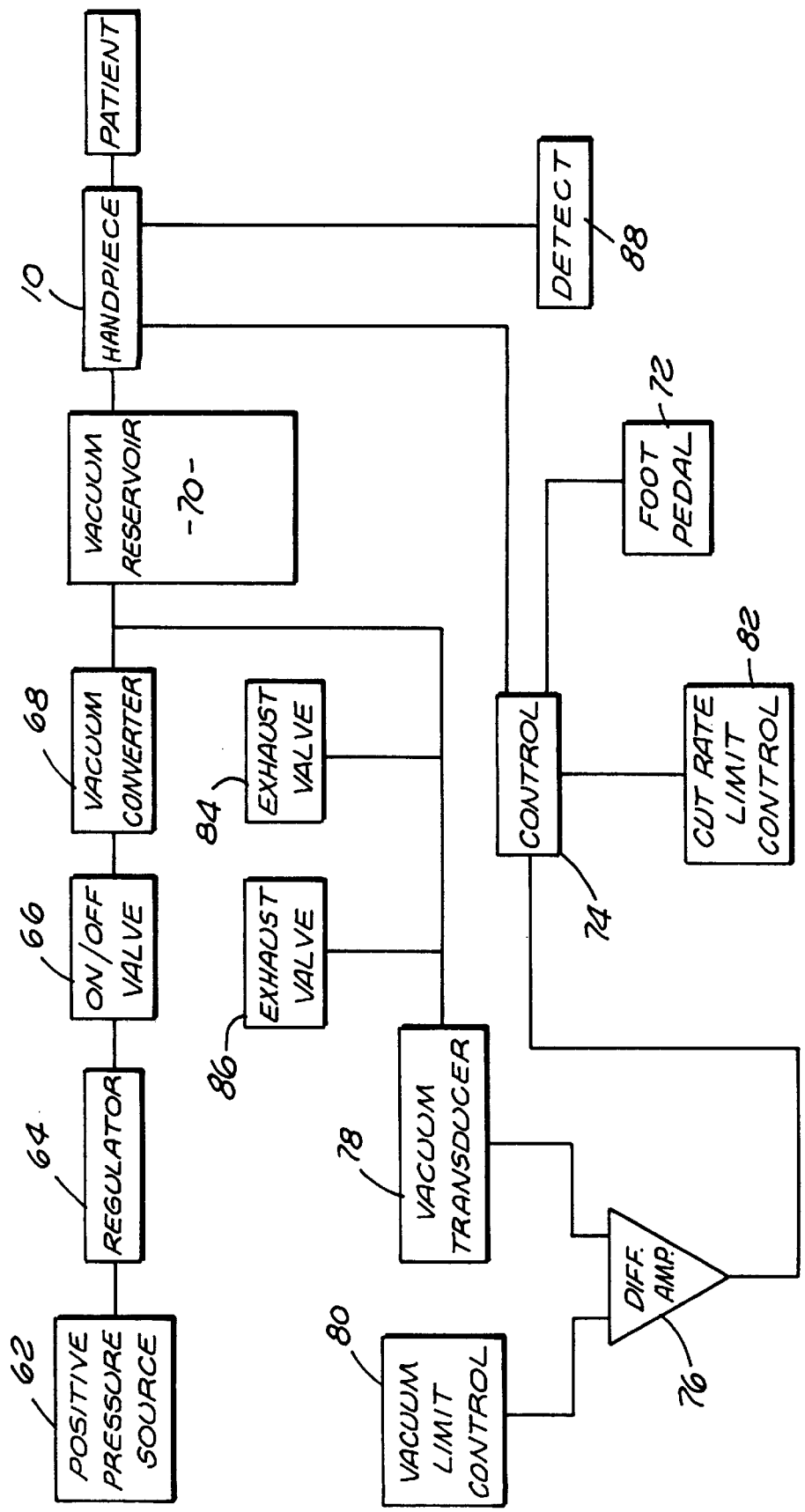

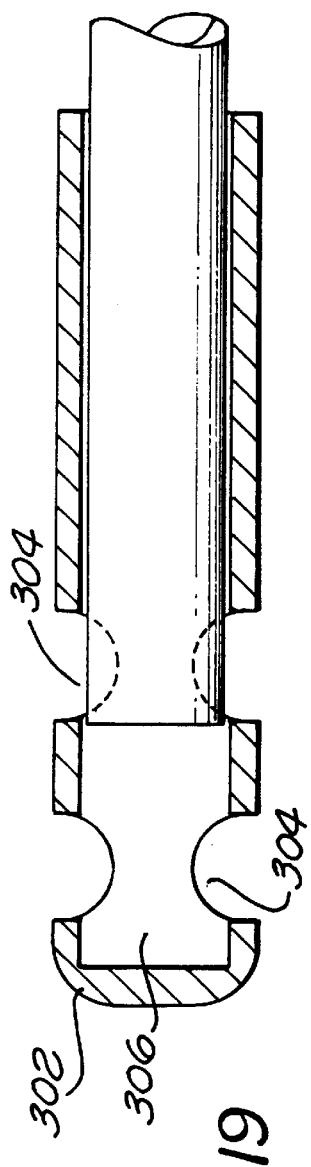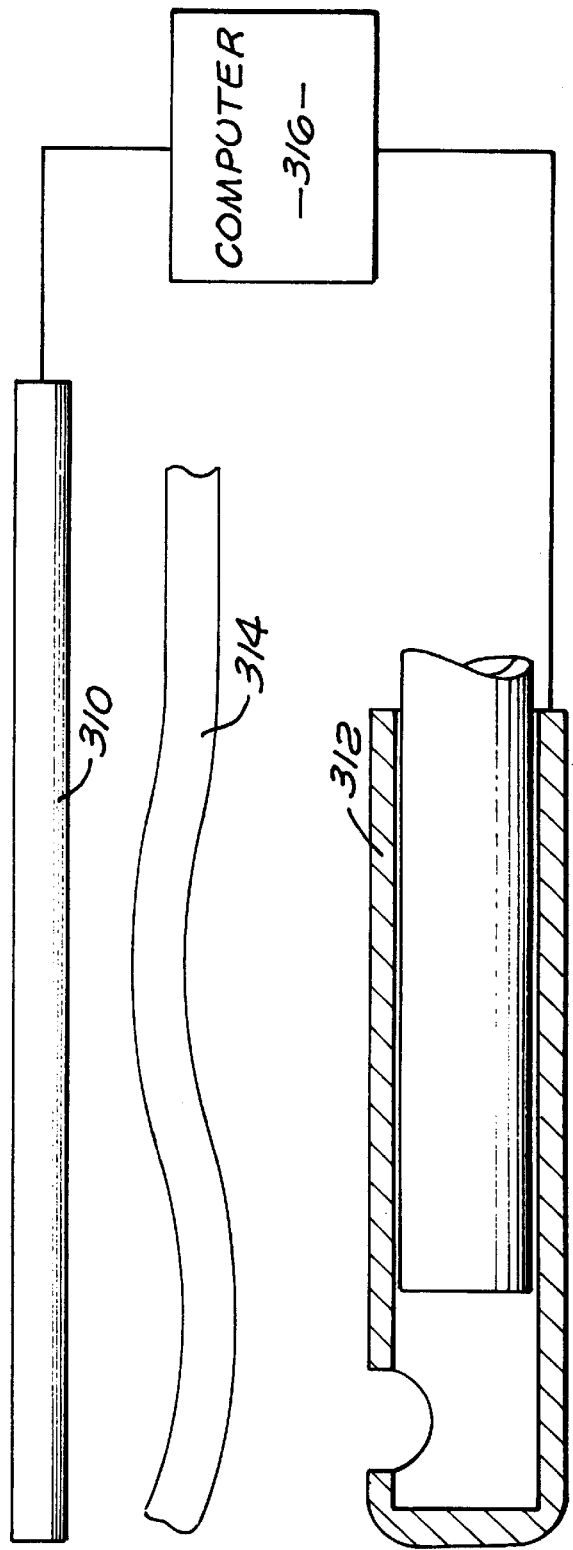

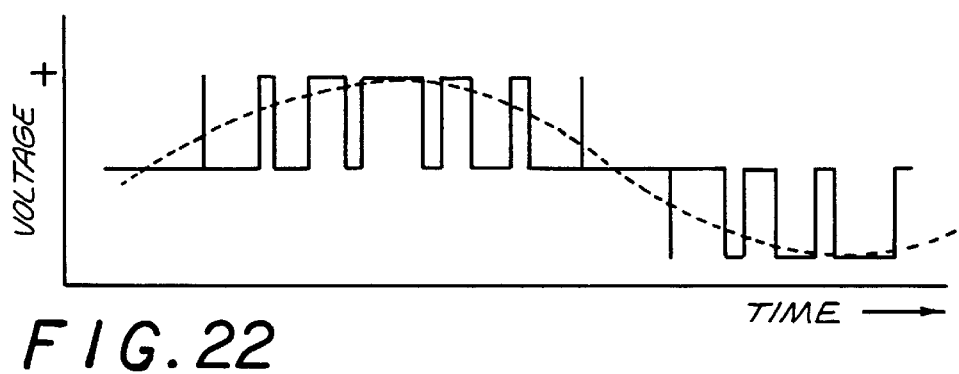
FIG. 22
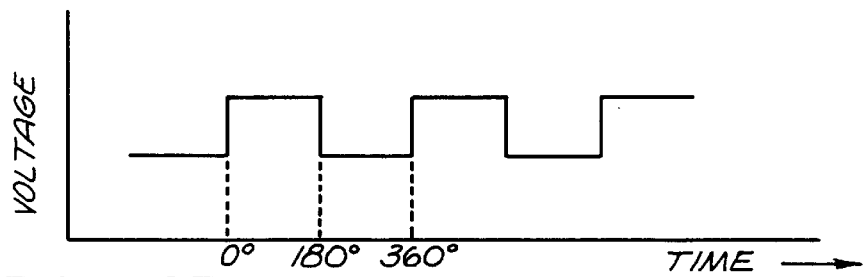
FIG. 23
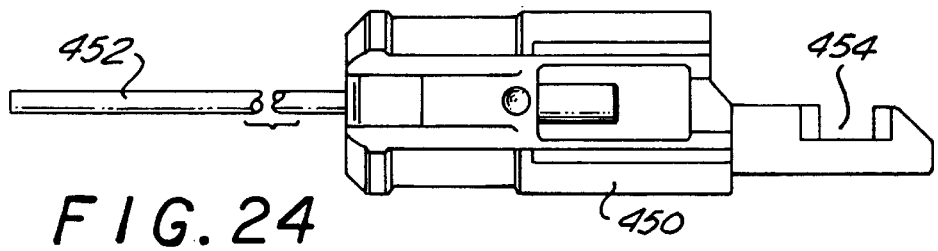
FIG. 24
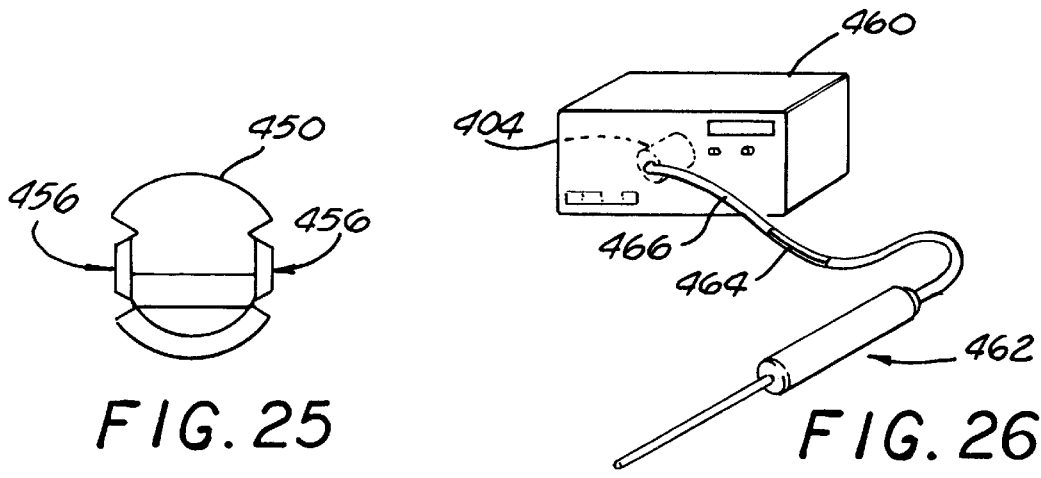
FIG. 25
FIG. 26

APPARATUS AND METHOD FOR PERFORMING OPHTHALMIC PROCEDURES

This application is a continuation-in-part of U.S. patent application Ser. No. 08/943,485 filed on Oct. 3, 1997.

BACKGROUND OF THE INVENTION

1. Field of the Invention

The present invention relates to a surgical system for cutting tissue.

2. Description of Related Art

There are many surgical procedures that require the cutting and aspiration of tissue. For example, in a retina re-attachment procedure the surrounding vitreo tissue must be removed before the retina is repaired. The cutting device must be delicate enough to remove the tissue without further damaging the retina. Prior art ophthalmic cutting devices include an inner sleeve that moves relative to an outer port of an outer sleeve. The sleeves are coupled to a vacuum system which pulls tissue into the outer port when the inner sleeve moves away from the port. The inner sleeve then moves in a reverse direction past the outer port to sever the tissue in a guillotine fashion. The vacuum system draws the severed tissue away from the outer port so that the process can be repeated.

The inner sleeve is driven by a motor located within a hand piece that is held by the surgeon. The inner sleeve is typically coupled to the motor by a rotating lever mechanism. Rotating lever mechanisms of the prior art are relatively large and complex. Additionally, the stroke and duty cycle of the inner sleeve is fixed for each device. It would be desirable to provide a surgical guillotine cutter that is inexpensive to produce, small in size and would allow a surgeon to vary the stroke and duty cycle of the inner cutter.

Guillotine cutters are typically provided with a control system that allows the surgeon to vary the vacuum pressure of the aspiration line. U.S. Pat. Nos. 4,395,258; 4,493,698; 4,706,687 and 4,838,281 issued to Wang et al. and Rogers et al., respectively, disclose systems for controlling the vacuum pressure of a guillotine cutter. The Wang/Rogers systems include a solenoid actuated valve that is coupled to the hand piece and controls the flow of fluid in the aspiration system. The position of the valve and the corresponding vacuum of the system is controlled by an input signal provided to the solenoid by a control circuit. The input signal is typically the summation of a feedback signal and a control signal that is generated by a potentiometer. The feedback signal corresponds to the actual vacuum pressure measured in the system. The potentiometer is typically a foot pedal that is manipulated by the surgeon.

The surgeon controls the vacuum pressure by depressing the foot pedal and varying the amount of air flow through the solenoid control valve. Because of the inertia within the system, there is typically a lag between the input command of the surgeon and the actual variation of vacuum pressure at the tip of the cutter. It would be desirable to provide a vacuum control system that has a more rapid response time than systems of the prior art.

Additionally, prior art guillotine cutters typically do not have many control functions, or safety features to prevent inadvertent damage to the eye. For example, prior art systems do not automatically compensate for variations in the load on the cutter. The surgeon must observe a reduction in cutting rate and then manipulate the cutter and the vacuum pressure to overcome the increased load. Additionally, with a prior art cutter, if the cutter ceases to operate while the vacuum pressure is applied to the system, the tissue may be pulled into the aspiration port of the outer sleeve. Such an event may damage the eye. It would be desirable to provide a guillotine cutter which has a number of control functions and safety features.

Cutting tissue sometimes causes undesirable bleeding which must be coagulated. Coagulation can be performed with an electro-cautery device. To coagulate the tissue the cutter is removed and an electro-cautery device is inserted into the patient. To continue cutting, the electro-cautery device must be removed to allow re-insertion of the cutter. Such a procedure is time consuming and may reduce the safety of the procedure. It would be desirable to provide a cutter that can also cauterize tissue.

SUMMARY OF THE INVENTION

The present invention is a surgical cutting system. The cutting system includes a cutter which has an inner sleeve that moves adjacent to an aspiration port of an outer sleeve. The inner sleeve is coupled to a source of vacuum that pulls tissue into the outer port when the inner sleeve is moved away from the port. The inner sleeve then moves across the outer port and severs the tissue in a guillotine fashion. The tip of the inner sleeve may exert a spring force that assist in the cutting action of the cutter.

The cutter includes a motor which creates an oscillating translational movement of the inner sleeve. The motor can be controlled by a controller that is coupled a foot pedal. The foot pedal and controller can be configured so that the motor decreases speed as the pedal is depressed by the operator.

The inner sleeve is coupled to an aspiration line that pulls the severed tissue out of the cutter. The level of the aspiration vacuum pressure can be controlled by a variable regulator valve. The regulator valve is coupled to the controller and the foot pedal. The foot pedal may have a switch that allows the system to operate in either a variable speed mode or a variable pressure mode. In the variable speed mode the actuation of the foot pedal changes the speed of the motor. In the variable pressure mode the actuation of the foot pedal changes the vacuum level within the aspiration line.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 1 is a cross-sectional view of surgical guillotine cutter of the present invention;

FIG. 2 is an enlarged cross-sectional view of the tip of the cutter;

FIG. 3 is an enlarged view similar to FIG. 2 showing tissue being drawn into an outer port of the cutter;

FIG. 4 is a an enlarged view similar to FIG. 2 showing an inner sleeve severing the tissue drawn into the outer port;

FIG. 5 is a schematic of a vacuum control system for the cutter;

FIG. 19 is a side view of a tip that has a plurality of aspiration ports;

FIG. 20 is side view showing a transmitter that tracks the location of a cutter within tissue;

FIG. 22 is graph showing input signals to a motor;

FIG. 23 is a graph showing a feedback signal from the motor;

FIG. 24 is a side view of a slider and an inner sleeve;

FIG. 25 is a bottom view of the slider;

FIG. 26 is a perspective view of an alternate embodiment of the system;

DETAILED DESCRIPTION OF THE INVENTION

Figure 6:
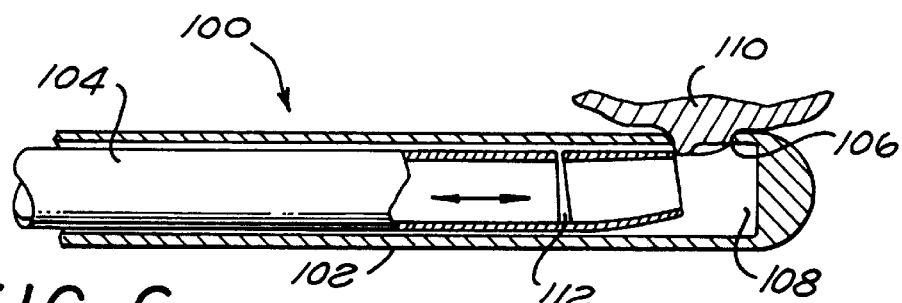
FIG. 6 is a side cross-sectional view of an alternate cutter.

Referring to the drawings more particularly by reference numbers, FIGS. 1 and 2 show a surgical guillotine cutter 10 of the present invention. The cutter 10 is used to remove and aspirate tissue. For example, the cutter 10 can be used to remove intraocular tissue during an ophthalmic procedure to re-attach a retina of an eye. Although use in an ophthalmic procedure is described, it is to be understood that the cutter 10 can be used to cut and aspirate other tissue, such as removing polyps, fibroids and other vascularized human tissue.

Referring to FIG. 2, the cutter 10 includes an outer sleeve 12 that has an outer port 14. The outer port 14 is in fluid communication with an inner channel 16 of the sleeve 12. Located within the inner channel 16 of the outer sleeve 12 is an inner sleeve 18. The inner sleeve 18 has an inner channel 20 that is in fluid communication with an aspiration system. The aspiration system creates a vacuum pressure that pulls tissue into the outer port 14 when the inner sleeve 18 is located away from the port 14. The inner sleeve 18 moves within the inner channel 16 of the outer sleeve 12 to cut tissue that is pulled into the outer port 14 by the aspiration system.

FIGS. 3 and 4 show tissue 22 that is cut by the cutter 10. The inner sleeve 18 is initially moved away from the outer port 14 and the vacuum pressure pulls tissue 22 into the port 14 and the inner channel 16. The inner sleeve 18 then moves toward the outer port 14 and severs the tissue 22 within the inner channel 16. The severed tissue is pulled through the inner channel 20 of the inner sleeve 18 by an aspiration system. The inner sleeve 18 then moves away from the outer port 14 wherein the cutting process is repeated.

The movement of the inner sleeve 18 also controls the flow of fluid through the outer port 14 and into the aspiration system. Increasing the cutting speed decreases the flow rate and vice versa. The flow of fluid through the opening 14 may vary the vacuum pressure within the aspiration system. In addition to varying the cutting speed the surgeon may also vary the vacuum pressure by changing the speed of the motor and the flow of fluid through the opening 14. The cutting device 10 of the present invention can thus control the vacuum pressure within the aspiration system by controlling the oscillation speed of the inner sleeve 14.

Referring to FIG. 1, the cutter 10 includes a motor 24 that is located within a hand piece 26. Extending from an end of the motor 24 is a rotating output shaft 28. The motor 24 is preferably an electrical device that is coupled to an external power source by wires 30 that are attached to a plug 32 screwed into the hand piece 26. The rotational speed of the output shaft 28 is a function of the amplitude of an input signal that is provided by wires 30. Although an electrical motor is described, it is to be understood that the motor may be a pneumatic device.

The cutter 10 has a wobble plate 34 that is attached to the output shaft 28 of the motor 24. The wobble plate 34 is located within a groove 36 of a slider 38. The slider 38 is attached to the inner sleeve 18. Rotation of the output shaft 28 spins the wobble plate 34, which induces an oscillating translational movement of both the slider 38 and the inner sleeve 18. The motor 24 and wobble plate 34 move the inner sleeve 18 in an oscillating manner to cut tissue as shown in FIGS. 3 and 4.

The slider 38 moves within a bearing sleeve 40 that is captured by an inner cap 42 and an outer cap 44 of the cutter 10. The outer cap 44 is screwed onto the hand piece 26. The slider 38 may have an aperture 46 that extends therethrough to allow air to flow out of the area between the slider 38 and the inner cap 42. The aperture 46 prevents the formation of a back pressure that may impede the movement of the slider 38. The slider 38 further has a channel 48 that is coupled to an aspiration line 50 by a tube 52. The channel 48 provides fluid communication between the aspiration line 50 and the inner channel 20 of the inner sleeve 18.

The stroke and the duty cycle of the inner sleeve 18 are related to the cam angle and profile of the wobble plate 34. The stroke and/or duty cycle can be varied by removing the cap 44 and replacing the wobble plate 34 with a new part which has a different cam angle and/or profile. The present invention thus allows a surgeon to readily change the duty cycle and stroke of the device 10.

FIG. 5 shows a system 60 for controlling the vacuum pressure within the cutter 10. The system includes a positive pressure source 62 which creates a positive pressure. The output of the positive pressure source 62 may be regulated by a regulator 64. The regulator 64 may be coupled to a shut-off valve 66 that can de-couple the source 62 from the remaining portion of the system 60. The wobble plate 34, slider 38 and outer cap 44 are preferably constructed from an electrically insulative material so that an electrical current does not flow from the handpiece to the patient. The wobble plate 34, slider 38 and outer cap 44 are preferably constructed from a molded plastic material.

The positive pressure created by the pump 62 is converted into a negative vacuum pressure by a converter 68. The converter 68 may be a venturi pump that is relatively linear in operation. The system 60 may have a reservoir 70 that is coupled to the converter 68 and the aspiration line 50 of the cutter 10. The converter 68 creates a vacuum pressure within the aspiration line 50 of the cutter 10, to pull the tissue into the outer port 14 of the outer sleeve 12, and to aspirate the severed tissue.

The system 60 includes a potentiometer 72 which provides a variable input signal to the motor 24 of the cutter 10. The potentiometer 72 is typically a foot pedal which can be manipulated by the surgeon to vary the input signal and the speed of the motor 24. Varying the speed of the motor 24 changes the oscillation frequency of the inner sleeve 18, the flow of fluid through the outer port 14 and the vacuum pressure within the system. The surgeon can therefore control the flow of fluid through the aspiration system by manipulating the foot pedal 72 and varying the motor speed of the cutter 10.

The potentiometer 72 may be coupled to the motor by a control circuit 74. The control circuit 74 is coupled to the output of a differential amplifier 76. One input of the differential amplifier 76 is coupled to a transducer 78 that senses the vacuum pressure within the system. The transducer 78 provides an output signal that corresponds to the magnitude of the vacuum pressure. The other input of the differential amplifier 76 may be connected to a vacuum limit control 80 which limits the level of the vacuum pressure. The differential amplifier 76 and transducer 78 provide a closed loop feedback signal for the aspiration system.

The control circuit 74 compares the feedback signal provided by the differential amplifier 76 with the control signal provided by the potentiometer 72 and generates the input signal for the aspiration system. The control circuit 74 typically adds, the difference between the feedback signal and the control signal from the foot pedal, to the control signal. The control circuit 74 may include a differential amplifier and adder connected as shown in U.S. Pat. No. 4,838,281, which is hereby incorporated by reference. The system 60 may include a variable cut rate limit control circuit 82 that limits the amplitude of the motor input signal and allows the surgeon to control the minimum and maximum cutting speed of the cutter 10.

The system 60 may have a first solenoid exhaust valve 84 that bleeds off the vacuum line to decrease the magnitude of the vacuum pressure. The valve 84 may be coupled to the control circuit 74 to lower the magnitude of the vacuum pressure when the actual pressure level exceeds a desired pressure level. The system 60 may also have a second solenoid exhaust valve 86 that quickly returns the system to atmospheric pressure. The shut-off valve 66 and second exhaust valve 86 can be coupled to the potentiometer 72 so that the shut-off valve 66 is closed and the exhaust valve 86 is opened when the surgeon releases the foot pedal 72 and moves the potentiometer to an off position. Returning the system to atmospheric pressure prevents a sudden vacuum surge when the surgeon again utilizes the cutter 10 at a surgical site.

The system 10 may also have an off detect circuit 88 which drives the motor 24 and moves the inner sleeve 18 to close the outer port 14 when the surgeon releases the foot pedal 72. Closing the outer port 14 prevents the residual vacuum of the system from pulling in tissue when the cutter 10 has been inactivated. The detect circuit 88 may drive one of the motor coils when the foot pedal is released to move the inner sleeve 18 to an extended position that closes the outer port 14.

In operation, a surgeon may insert the outer sleeve 12 into an eye to perform an ophthalmic procedure. The surgeon may remove intraocular tissue by depressing the foot pedal 72 and initiating the cutting action of the cutter 10. The cutting speed and fluid flow can be varied by manipulating the foot pedal 72 and varying the motor speed of the cutter. Valving the vacuum pressure at the outer port 14 of the cutter provides an almost instantaneous response time for varying the fluid flow at the surgical site. Releasing the foot pedal 72 closes the shut-off valve 66 and opens the exhaust valve 88 to return the system 60 to atmospheric pressure.

By way of example, the aspiration line 50 and/or reservoir 70 may be directly coupled to the intake port of a linear pump. The potentiometer 72 and/or control circuit 74 may provide an input signal to control the output of the linear pump and the vacuum pressure within system. The linear pump may be a device sold by Medo of Woodale, Ill. under the part designation VP0660. In this embodiment, the vacuum pressure may also be further regulated by controlling the motor speed of the cutter 10.

Although a control circuit 74 is shown and described, it is to be understood that the foot pedal 72 can be connected directly to the motor 24 without a feedback input. Additionally, although a foot pedal 72 is shown and described, it is to be understood that the motor 24 could be controlled by a handpiece or other input device.

FIG. 6 shows an alternate embodiment of a cutter 100. The cutter 100 includes an outer sleeve 102 and an inner sleeve 104. The outer sleeve 104 has an aspiration port 106 that is in fluid communication with an inner channel 108. The inner sleeve 104 is driven in a reciprocating manner by a motor (not shown). Movement of the inner sleeve 104 cuts tissue 110 that is pulled into the aspiration port 106.

The inner sleeve 104 has a circumferential slit 112 that allows the distal end of the sleeve 104 to bend toward the aspiration port 106 when engaging and cutting the tissue 110. The bending of the inner sleeve 104 assist in cutting the tissue 110.

Figure 7:
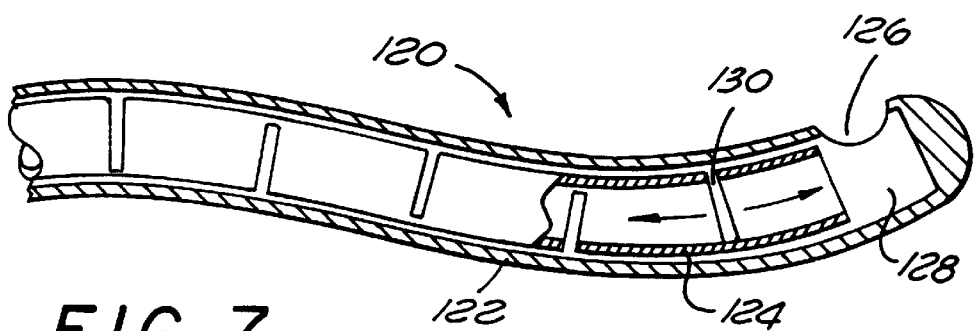
FIG. 7 is a side cross-sectional view of an alternate cutter.

FIG. 7 shows another embodiment of a flexible cutter 120 which has a flexible outer sleeve 122 and a flexible inner sleeve 124. The outer sleeve 122 has an aspiration port 126 that is in fluid communication with an inner channel 128. The outer sleeve 122 is preferably constructed from a flexible plastic or curved metal material that can bend and conform to the shape of a body passage or cavity. The inner sleeve 124 is preferably constructed from a metal material that can cut tissue pulled into the aspiration port 126.

The inner sleeve 124 has a plurality of circumferential slits 130 that reduce the stiffness of the sleeve 124. The slits 130 allow the inner sleeve 124 to follow the shape of the outer sleeve 122. The most distal slit 130 allows the distal end of the inner sleeve 124 to bend into the aspiration port 126 to assist in the cutting of the tissue 110. The flexible cutter 120 can function as a cutting catheter that is inserted into cavities and passages of a body. For example, the flexible cutter 120 can be used to cut polyps, fibroids and other vascularized human tissue.

Figure 8:
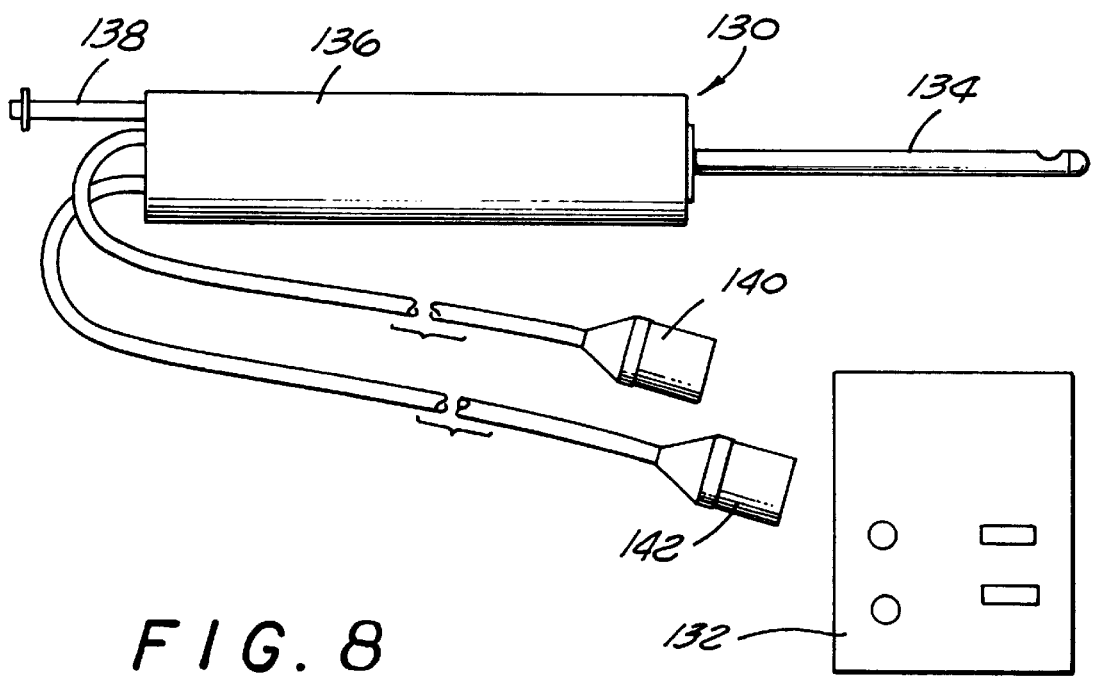
FIG. 8 is a perspective view of a cutter system of the present invention which has an electrical generator coupled to a cutter.

FIG. 8 shows a cutter 130 coupled to a radio frequency (RF) electrical generator 132. The cutter 130 includes a tip 134 that is connected to a motor (not shown) located within a handpiece 136. The handpiece 136 has an aspiration line 138 that is coupled to a vacuum source (not shown). The handpiece 136 is coupled to the generator 132 by a pair of connectors 140 and 142. One of the connectors 140 provides power to the motor. The other connector 142 supplies electrical energy to the tip 134 so that the surgeon can cauterize tissue with the cutter 130. The electrical energy may be controlled by a foot pedal (not shown) that can be manipulated by the surgeon.

A surgeon can thus both cut and cauterize tissue with the same device. By way of example, the cutter 130 may be used to cut polyps or fibroids in a laparoscopic procedure. The generator 132 may have a plurality of control functions that allow the surgeon to vary the frequency, pulse rate or time duration of electrical energy provided to the cutter 130.

Figure 9:
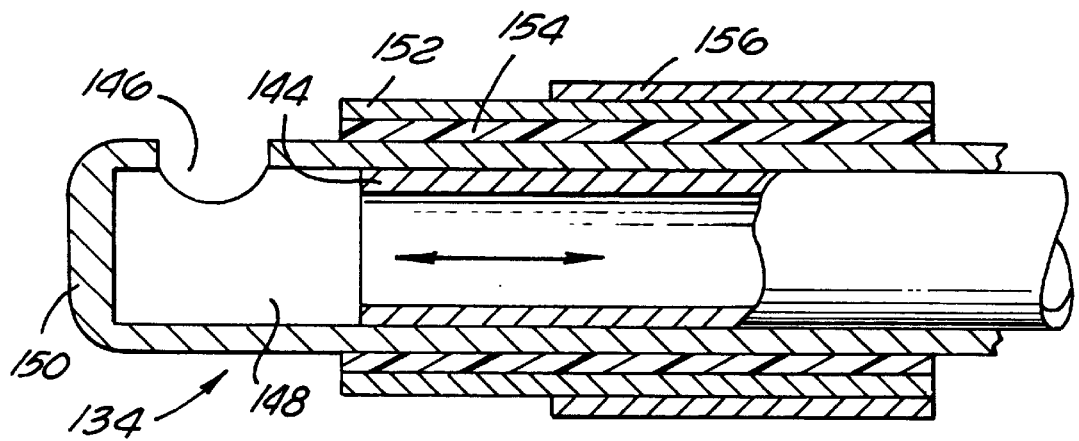
FIG. 9 is an enlarged view of a cutter tip which functions as an electrode.

FIG. 9 shows the cutter tip 134 constructed as an electrode. The tip 134 has an inner sleeve 144 that reciprocates across an aspiration port 146 within an inner channel 148 of an outer sleeve 150. The tip 134 also has an outer conductive layer 152 that is separated from the outer sleeve 150 by a layer of insulation 154. The outer conductive layer 152 is covered with an layer of insulation 156. The outer sleeve 150 and outer conductive layer 152 are connected to electrical terminals of the generator 132. Electrical current flows through tissue between the outer sleeve 150 and the outer conductive layer 152.

As an alternate embodiment, the inner sleeve 144 can be connected to the generator 132 instead of the outer sleeve 150. The cutter 130 may then provide pulses of current to the tissue as the inner sleeve 144 reciprocates across the aspiration port 146. The system may also have a voice system which provide input on the present mode of the system. By way of example, the system may provide an audio indication that the electro-cautery function is active, or provide an audio indication that the some component was not set-up or assembled correctly.

Figure 10:
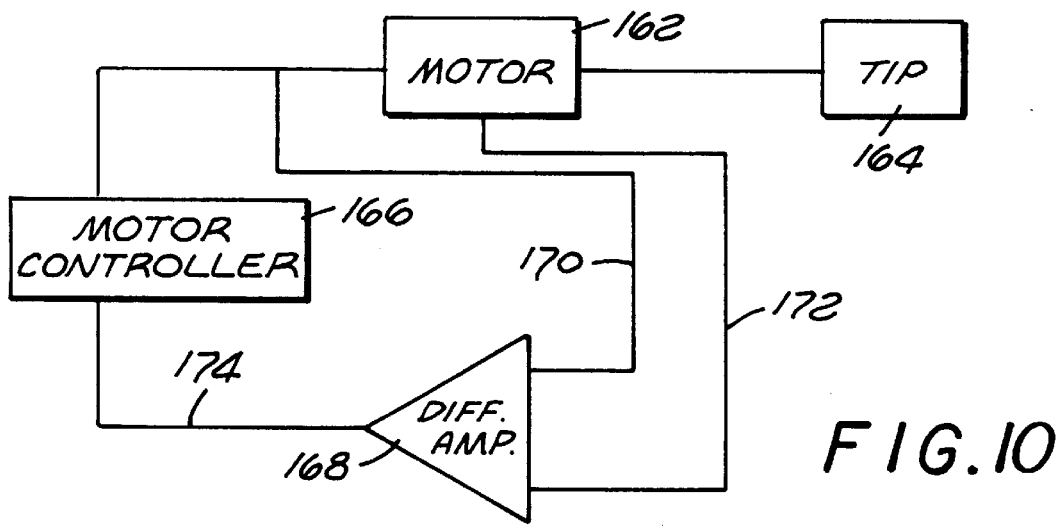
FIG. 10 is a schematic of a system for controlling the motor speed of a cutter.

FIG. 10 is a schematic of a system 160 which controls the motor speed of a motor 162 and a tip 164. In general the system 160 provides more power to the motor 162 with an increase in the load on the tip 164. For example, when the tip 164 engages a more fibrous tissue, the resistance of the tissue will slow down the tip 164 and the motor 162. The system 160 senses the reduction in speed and automatically increases the power to the motor 162.

The motor 162 is preferably a brushless DC motor device which contains three coils that drive an internal rotor (not shown). The system 160 includes a motor controller 166 that provides power to the motor 162. The motor controller 166 preferably provides three sinusoidal drive signals to the coils of the motor 162. The sinusoidal signals provide a relatively smooth control of the motor.

The system 160 has a differential amplifier 168 that senses the input voltage of the motor 162 on line 170 and the output current of the motor 162 on line 172. The output of the differential amplifier provides a feedback control signal to the motor controller 166 on line 174. The system 160 monitors the speed of the motor 162 by sensing the output current. It being understood that the current may increase or decrease with a change in motor speed. The system 160 varies the input voltage to the motor 162 to maintain a constant voltage to current ratio and compensate for different loads on the motor. Although a differential amplifier is shown and described, it is to be understood that the system may control the power provided to the motor as a function of speed in a variety of ways. For example, the motor may contain a Hall sensor that directly measures the speed of the motor and provides a feedback signal that is processed by the motor controller 166 to increase power with a reduction in motor speed.

Figure 11:
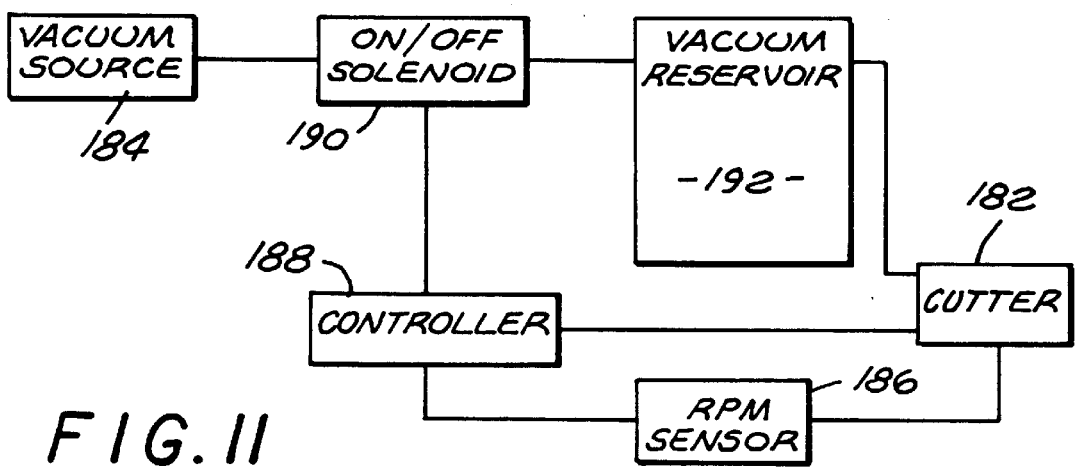
FIG. 11 is a schematic of a system that terminates the vacuum supply when the cutter no longer cuts.

FIG. 11 shows an alternate embodiment of a system 180 which automatically disconnects the cutter 182 from a vacuum source 184 when the cutter 182 is no longer cutting. The system 180 prevents the vacuum source 184 from pulling tissue into the aspiration port of the cutter 182 when the inner sleeve is no longer reciprocating relative to the port. Continued aspiration while the cutter 182 is no longer properly functioning may result in tissue damage.

The system 180 includes a speed (RPM) sensor 186 which senses the speed of the cutter motor. The sensor 186 provide a feedback signal to a controller 188. The controller 188 controls a solenoid actuated on/off valve 190 located between the vacuum source 184 and a vacuum reservoir 192. When the motor speed falls below a threshold level the controller 188 drives the valve 190 to an off position to terminate the flow of aspiration fluid from the cutter. When the cutting speed increases above the threshold value the controller 188 opens the valve 190 to resume normal operation.

Figure 12:
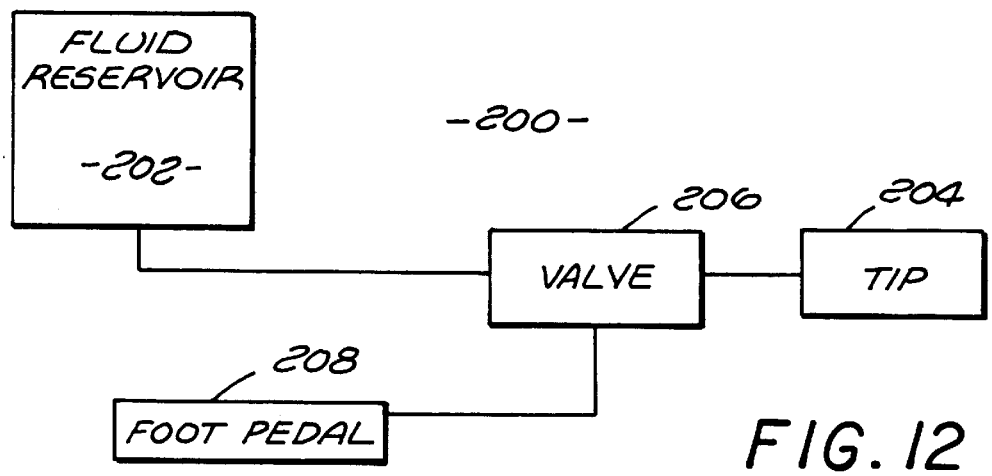
FIG. 12 is a schematic of a system that can terminate a flow of irrigation fluid.

FIG. 12 shows a fluid irrigation system 200 that provides irrigation fluid to the patient. In an ophthalmologic procedure the irrigation fluid is typically introduced to the cornea through a secondary incision. The system 200 includes a fluid reservoir 202 that typically provides fluid through the force of gravity to a tip 204 located within the patient. The flow of irrigation fluid from the fluid reservoir 202 to the patient is controlled by a valve 206. The valve 206 may be a solenoid actuated on/off device that is controlled by a foot pedal 208. The foot pedal 208 can be manipulated by the surgeon to control the flow of irrigation fluid to the patient. As an alternate embodiment, the valve 206 may be a proportional device that allows the surgeon to control the amount of irrigation fluid that flows to the patient.

Figure 13:
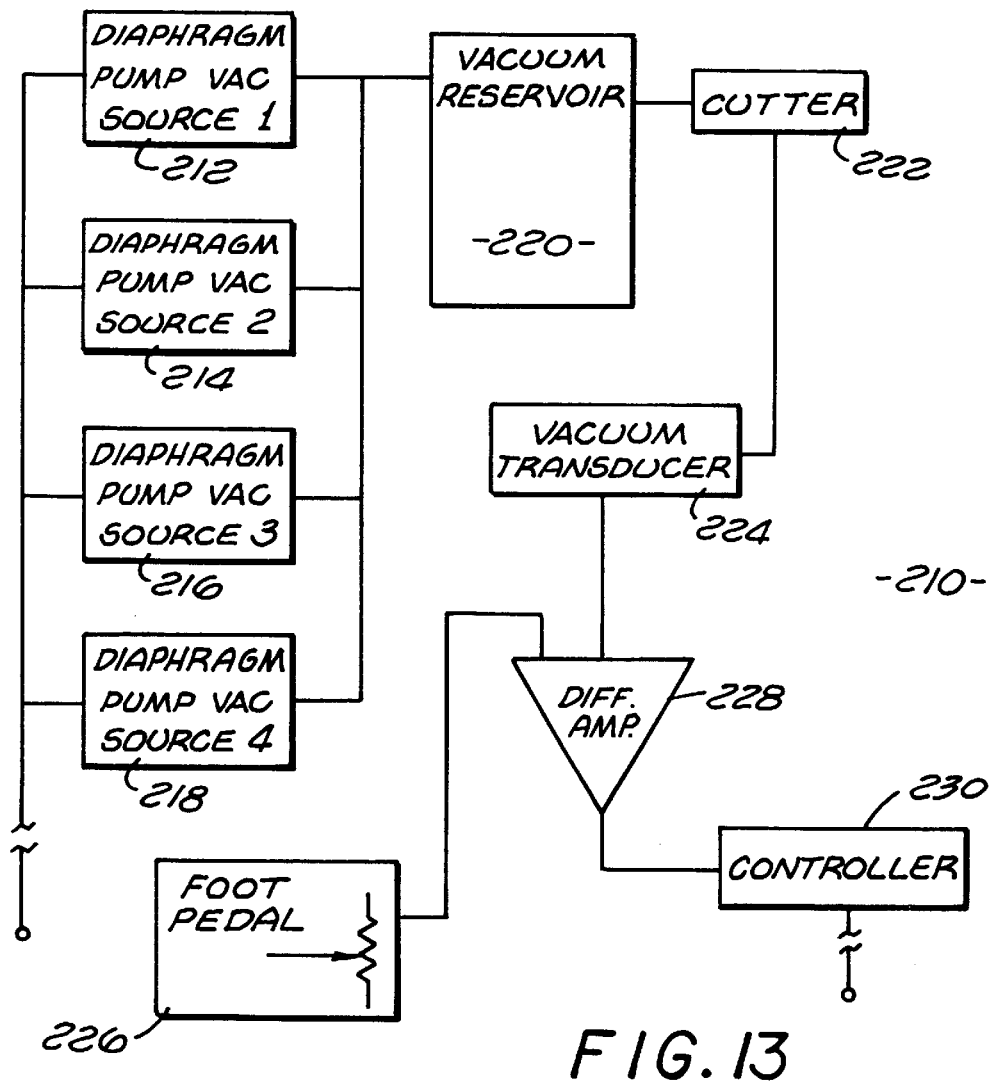
FIG. 13 is a schematic of a system which contains a plurality of vacuum pumps.

FIG. 13 shows a vacuum control system 210 that contains a plurality of vacuum sources 212, 214, 216 and 218 connected in parallel with a vacuum reservoir 220 and a cutter 222. The multiple vacuum sources are actuated sequentially to provide greater flowrate and sensitivity than a single unit system.

The system 210 includes a vacuum transducer 224 that senses the vacuum pressure provided to the cutter 222, and a foot pedal 226 that allows the surgeon to control the vacuum pressure. The output of the transducer 224 and the foot pedal 226 are provided to a differential amplifier 228. The amplifier 228 provides an error signal that is processed by a controller 230. The controller 230 provides control signals to actuate and control the vacuum sources 212, 214, 216 and 218. In the preferred embodiment, the vacuum sources are variable speed diaphragm vacuum pumps.

In operation, the controller 230 may actuate and drive one of the pumps 212, 214, 216 or 218. The surgeon may request a lower vacuum pressure by depressing the foot pedal 226. Depressing the foot pedal 226 varies the error signal provided by the differential amplifier 228. The controller 230 processes the error signal and actuates, or changes the speed, one or more of the inactive vacuum pumps to decrease the vacuum pressure provided to the cutter 222. Further depressing the foot pedal may induce the actuation of the other pumps and so forth and so on. The controller 230 may also vary the speeds of the pumps 212, 214, 216 and 218 to further obtain a desired vacuum level. As an alternate embodiment, the system may have a plurality of orifices that each have a different diameter. The different orifices can be coupled to one or more pumps.

Figure 14:
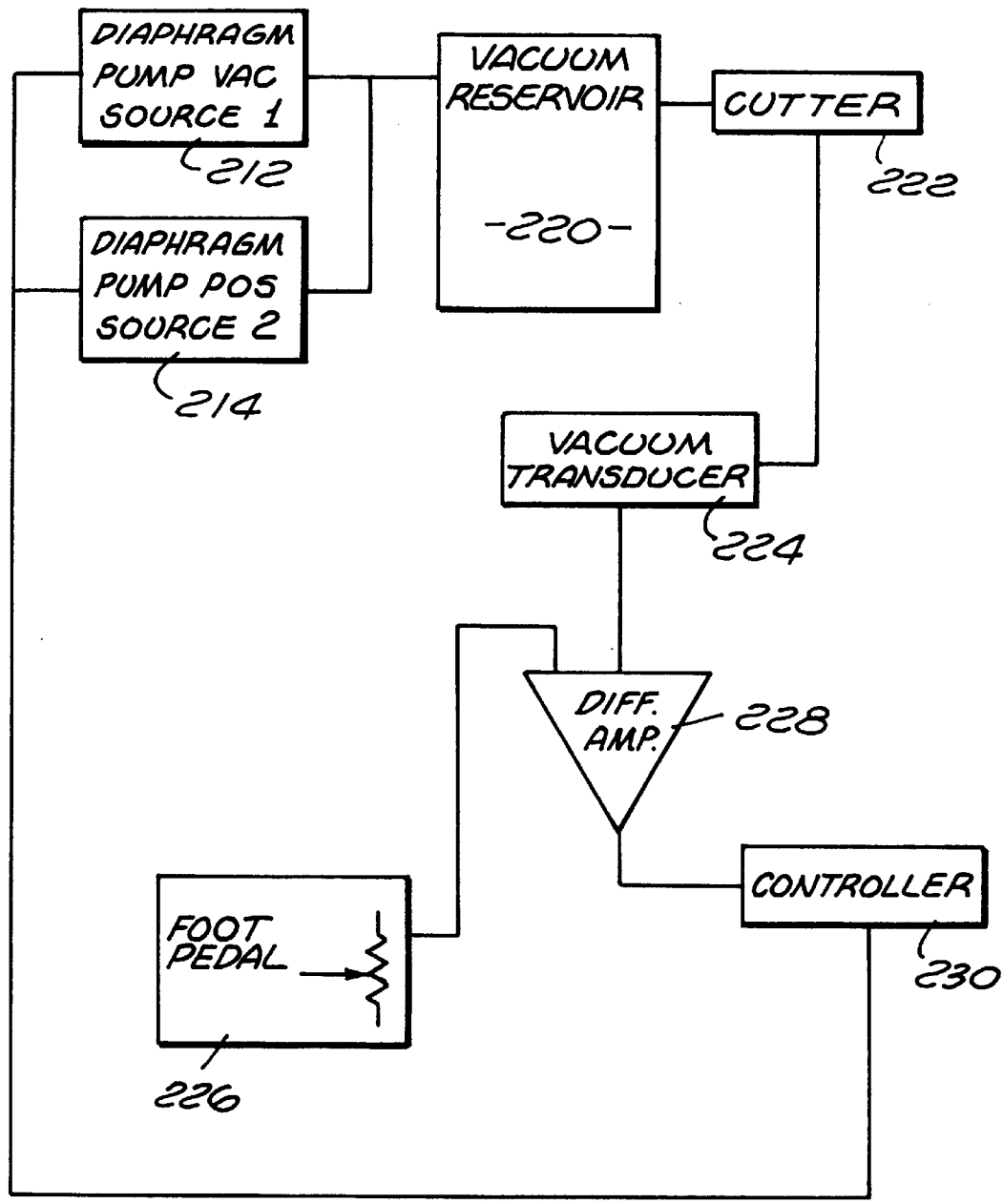
FIG. 14 is a schematic of a system that contains a vacuum pressure pump and a positive pressure pump.

FIG. 14 shows an alternate embodiment of the system shown in FIG. 13. The intake and exhaust lines of pump 214 are switched so that the pump provides a positive pressure to the vacuum reservoir 220. The positive pressure source 214 allows the controller 230 to rapidly increase the pressure within the system when the surgeon releases the foot pedal 226. The push-pull dual pump configuration provides a vacuum system with a quick response to commands for increasing or decreasing the vacuum pressure.

Figure 15:
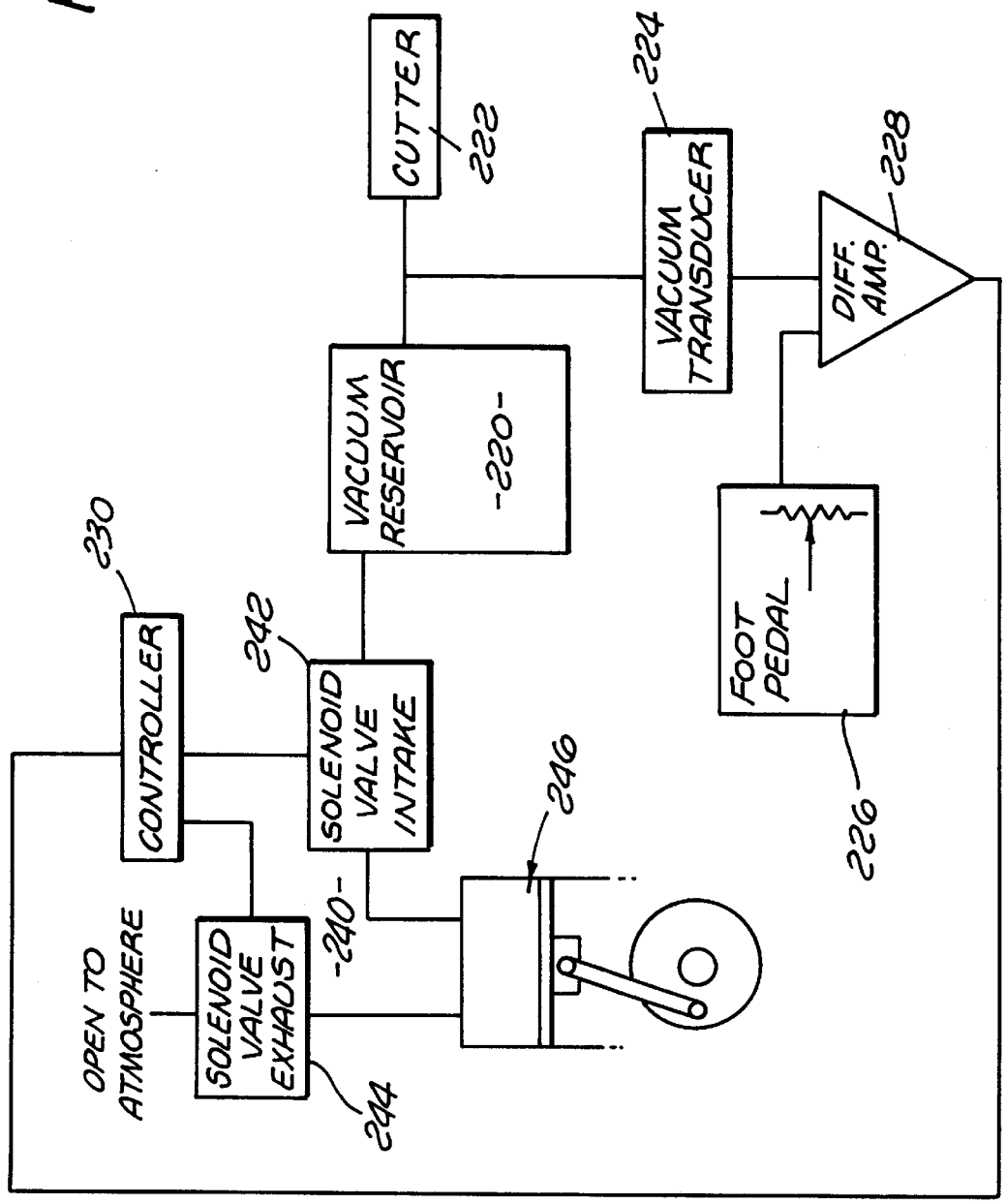
FIG. 15 is a schematic of a system that contains a pump which has electronically controlled intake and exhaust valves.

FIG. 15 is another alternate embodiment of a vacuum system with an electronically controlled pump assembly 240. The pump assembly 240 includes an intake valve 242 and an exhaust valve 244 that control the flow of fluid from a pumping assembly 246. The pump assembly 246 may contain a flexible diaphragm or piston that pumps fluid within an internal pumping chamber of the assembly. The intake valve 242 is open during an intake stroke of the pumping assembly 246 and closed during an exhaust stroke of the assembly 246. Conversely, the exhaust valve 244 is closed during the intake stroke and open during the exhaust stroke.

The valves 242 and 244 are preferably solenoid actuated devices that are driven by the controller 230. The controller 230 can vary the timing on the opening and closing of the valves 242 and 244 to control the flowrate through the pump assembly 246 and the vacuum pressure provided to the cutter 222. As an alternate embodiment, the valves 242 and 244 may be proportional devices that allow the controller 230 to control the flowrate and vacuum pressure of the system.

Figure 16:
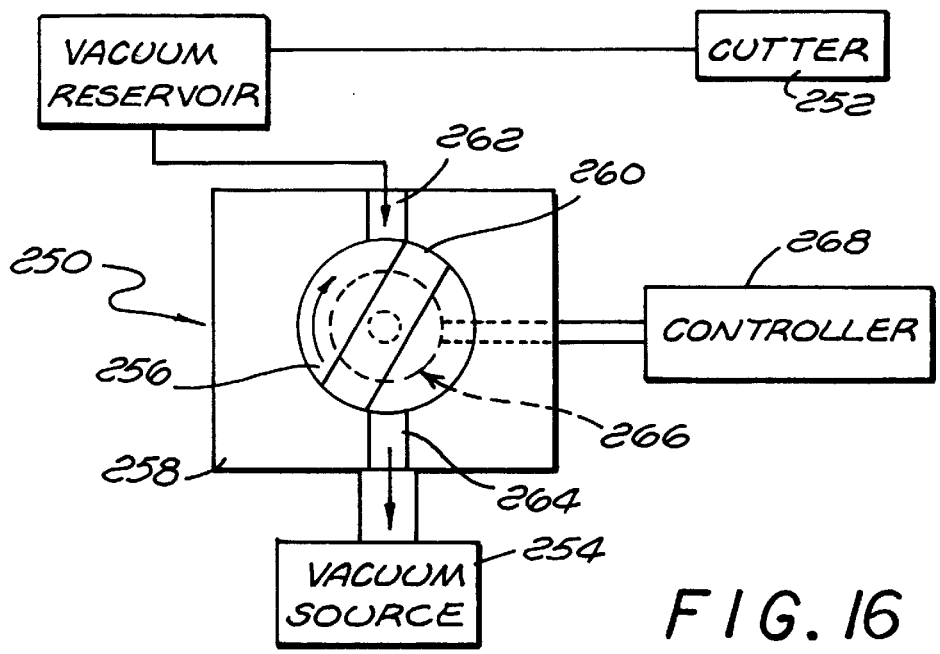
FIG. 16 is a schematic of a rotary valve that controls the flow of aspiration fluid.

FIG. 16 is a valve 250 that can control the vacuum pressure provided to a cutter 252 from a vacuum source 254 and reservoir 255. The valve 250 includes a core 256 that rotates within a valve housing 258. The core 256 has an inner channel 260 that periodically becomes aligned with an inlet port 262 and an outlet port 264 of the valve housing 258. Fluid flows through the valve 250 when the inner channel 260 is aligned with the ports 262 and 264. The core 256 can be rotated by a motor 266 that is controlled by a controller 268. The motor 266 can vary the rotational speed of the core 256. Varying the core speed changes the flowrate through the valve 250 and the vacuum pressure provided to the cutter 252. The valve 250 can be utilized in a system that does not control the vacuum pressure by varying the speed of the cutter.

Figure 17:
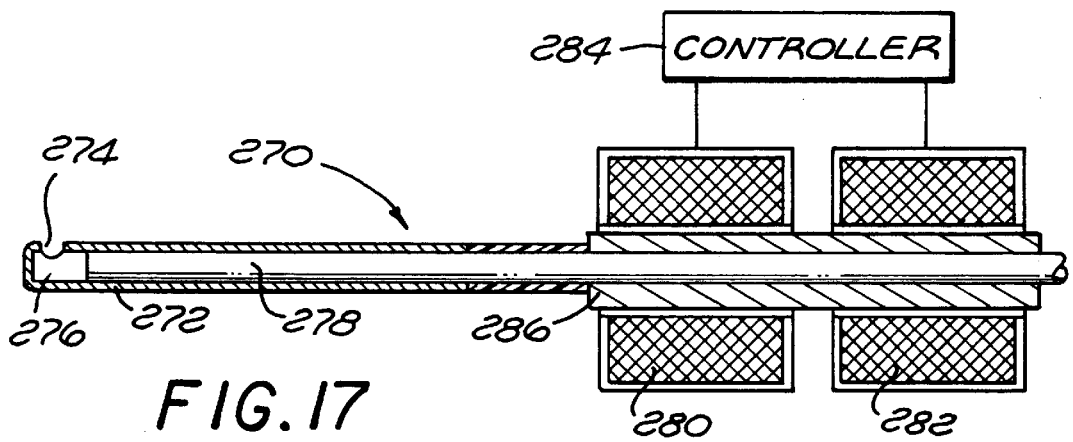
FIG. 17 is a schematic showing a solenoid driven guillotine cutter.

FIG. 17 is an alternate embodiment of a variable port cutter 270. The cutter 270 includes an outer sleeve 272 that has an aspiration port 274 in fluid communication with an inner channel 276. An inner sleeve 278 is located within the inner channel 276 of the outer sleeve 272. Mounted to the outer sleeve 272 is a first solenoid 280 and a second solenoid 282. The solenoids 280 and 282 are connected to a controller 284 and coupled to the outer sleeve 272 by a magnetic core 286.

The controller 284 provides a current to one of the solenoids 280 and 282 which creates a electromagnetic force on the inner sleeve 272. The first solenoid 280 is wound to move the inner sleeve 278 toward the aspiration port 274. The second solenoid 282 moves the sleeve 278 away from the port 274. The controller 284 sequentially drives the solenoids 280 and 282 to reciprocate the inner sleeve 278 across the aspiration port 274. The controller 284 can provide control signals to the solenoids 280 and 282 to control how far the inner sleeve 278 moves across the port 274 and the size of the aspiration opening. For example, the controller 284 may control the solenoids so that the inner sleeve 278 moves only half-way across the aspiration port 274. The variation in sleeve movement will change the flowrate within the inner channel 276.

Figure 17A:
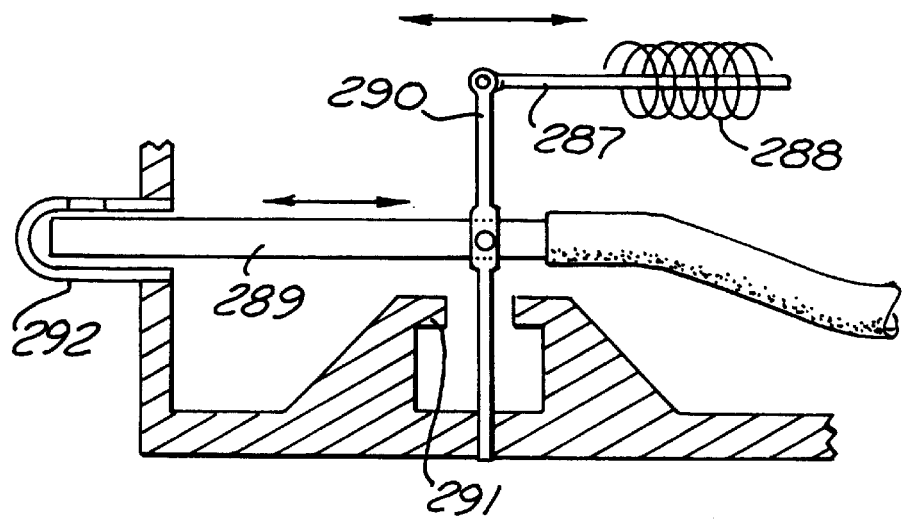
FIG. 17a is a schematic of a solenoid that is coupled to an inner sleeve of a cutter by a spring.

FIG. 17a shows another embodiment of a surgical cutter which has a single solenoid. The solenoid includes an armature 287 that moves relative to a coil 288. The armature 287 is coupled to an inner sleeve 289 by a cantilevered spring 290. The movement of the spring 290 is limited by a stop 291. The stop 291 also limits the movement of the inner sleeve 289 relative to the outer sleeve 292. The stop 291 prevents the inner sleeve 289 from striking the end of the outer sleeve 292.

In operation, the coil 288 is energized to move the armature 287. The armature 287 moves the spring 290 and the inner sleeve 289. When the coil 288 is de-energized the spring 290 moves the inner sleeve 289 back to the original position. As an alternate embodiment the coil 288 may move relative to a stationary magnet.

Figure 18:
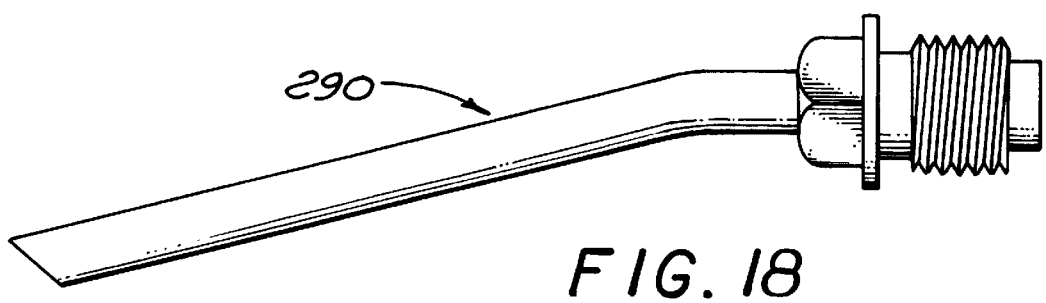
FIG. 18 is a side view of a bent tip.

FIG. 18 shows a tip 295 which has a bend at the proximal end. When inserted through an incision to perform an ophthalmic procedure, the bent tip 295 may provide more transverse energy to the eye without damaging the incision. The bent tip 295 may utilize the flexible inner sleeve shown in FIG. 7.

FIG. 19 shows an alternate embodiment of a cutter 300 which has an outer sleeve 302 that has a plurality of aspiration ports 304 that are in fluid communication with an inner channel 306. The cutter 300 further has an inner sleeve 308 that is reciprocated by a motor (not shown) to cut tissue pulled into the aspiration ports. The multiple aspiration ports 304 are desirable when removing large amounts of tissue. By way of example, such a cutter 300 would be preferable when performing a liposuction procedure.

FIG. 20 shows a transmitter 310 that monitors the location of a cutter 312 placed within tissue 314. The transmitter 310 may provide audio frequency (sonar) waves that are received by the cutter 312. The transmitter 310 and cutter/receiver 312 can be coupled to a computer 316 which processes the transmitted signals to determine the location of the cutter 312 within the tissue 314.

Figure 21:
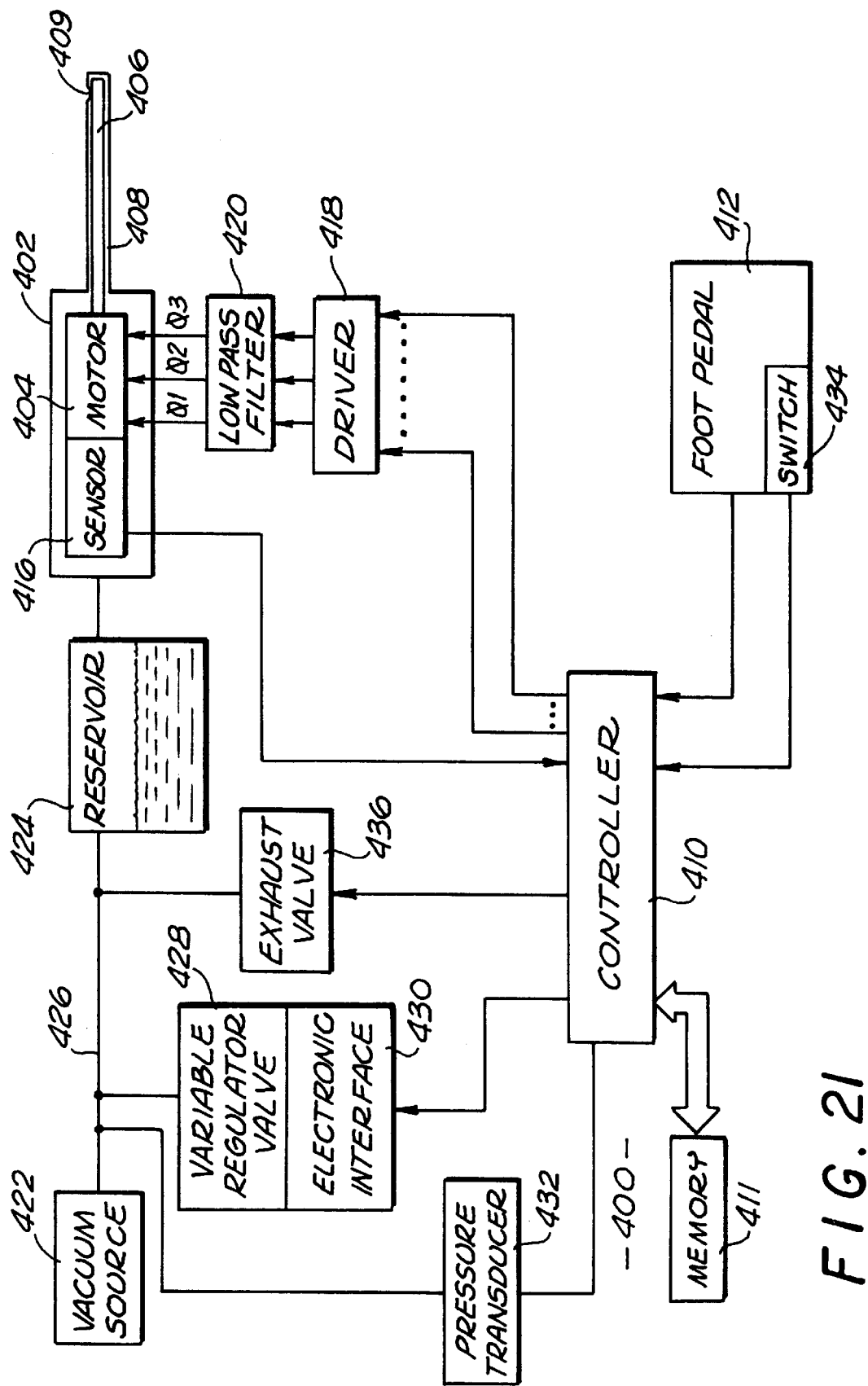
FIG. 21 is a schematic of an alternate embodiment of the system.

FIG. 21 shows an alternate embodiment of a surgical system 400. The system 400 may include a handpiece 402 which contains a variable electric motor 404 that moves an inner sleeve 406 relative to an outer sleeve 408. The outer sleeve 408 has an aspiration port 409. The inner sleeve 406 can be coupled to the motor 404 by a wobble plate and slider assembly that is the same or similar to the configuration depicted in FIG. 1.

The motor 404 is coupled to a controller 410. The controller 410 can be a microprocessor that is coupled to a memory device(s) 411. The controller 410 performs software routines and computations in accordance with instructions retrieved from memory 411. The instructions may be embedded in ROM, stored on a mass storage device and/or retrieved from an external source such as a floppy disk, and/or downloaded from a network.

The controller 410 is coupled to a foot pedal 412. The foot pedal 412 can be depressed from an upward position to a downward position. The foot pedal 412 may contain a microprocessor (not shown) which generates digital signals that are transmitted to an RS-232 interface (not shown) coupled to the controller 410. The controller 410 interprets the input signal(s) from the foot pedal 412 and provides output signals to drive the motor 404, typically in accordance with a software routine. Alternatively, the foot pedal 412 may have a potentiometer or other sensor (not shown) that provides an output signal which varies with the position of the pedal.

In one embodiment, the software routine of the controller 410 provides output signals so that the motor 404 and inner sleeve 406 are moving at a maximum speed when the pedal 412 is in the upward position. By way of example, the maximum speed may be 2500 cuts per minute (cpm). The software routine may be such that the controller 410 reduces the speed of the motor 404 when the foot pedal 412 is depressed by an operator. The foot pedal 412 can be depressed to a point where the motor 404 operates at a minimum speed. By way of example, the minimum speed may be 1000 cpms. The upper and lower speed limits may be adjustable through a control button(s) (not shown) on a console (not shown) that houses the electronics of the system. Providing the maximum cutting speed at the released position of the foot pedal 412 insures that the inner sleeve 406 is operating at a safe condition when the operator releases the pedal. At slower speeds the cutter tends to pull and tear tissue. The motor 404 may be turned off when the operator releases the foot pedal 412. A slight depression of the pedal 412 energizes the motor 404 to the maximum speed. A further depression of the pedal reduces the speed of the motor 404.

The controller 410 may be coupled to the motor 404 by a source sink driver circuit 418 and a low pass filter 420. Although one controller 410 is shown and described, it is to be understood that there may be an additional controller (not shown) that is dedicated to the motor 404 and coupled to the driver circuit 418 and a main controller. The source sink driver 418 provides output signals that correspond to the different phases Ø1, Ø2 and Ø3 of the motor 404. The low pass filter 420 filters the output of the driver circuit 418. The controller 410 provides output signals to the driver 418 which define the shape of the waveform generated by the circuit 418.

FIG. 22 shows an output waveform for one phase of the driver circuit 418. The processor controlled driver circuit 418 may initially provide a short pulse separated from a longer pulse by a relatively long interval. The driver circuit 410 provides a series of gradually increasing pulses separated by gradually decreasing time intervals until a maximum pulse is provided to the motor 404. The driver circuit 410 then provides a series of gradually increasing pulses separated by gradually increasing time intervals. The low pass filter 420 filters the output of the driver circuit 418 to create the sine-wave (shown in dashed lines) which is provided to the motor 404. The controller 410 can thus control the motor 404 without a digital to analog (D/A) converter.

As shown in FIG. 21, the motor 404 may have a sensor 416 that provides a motor position feedback signal to the controller 410. The controller 410 may utilize the feedback information in computing the output signals for the motor 404. The software routine may be such that the controller 410 drives the motor 404 so that the inner sleeve 406 is at a predetermined start and/or stop position relative to the outer sleeve 408. By way of example, the inner sleeve 406 may be stopped in a position to close the port 409 of the outer sleeve, or stopped in a position that opens the outer sleeve port, or any other intermediate position. The start position may be the same as the stop position.

Figure 22A:
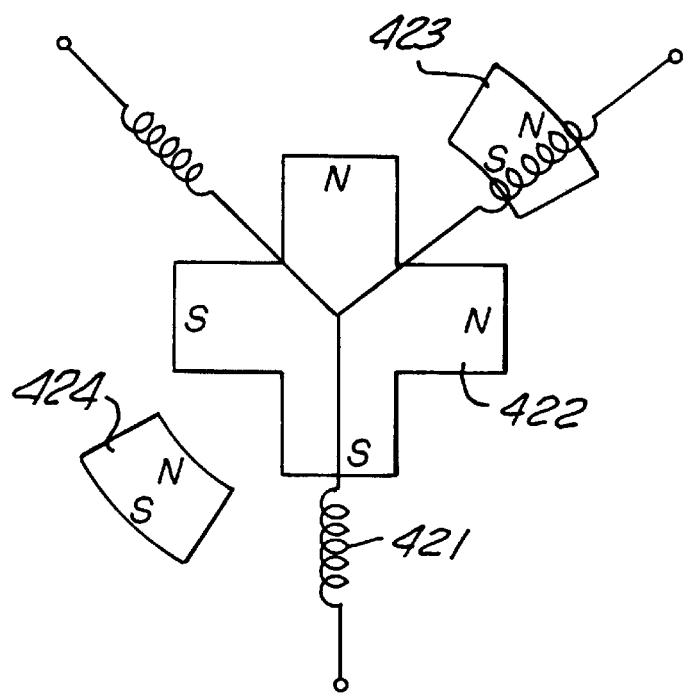
FIG. 22a is a schematic view of a stop mechanism for a motor of the cutter.

As shown in FIG. 22a, the motor 404 may contain three coils 421 and a four pole magnetic rotor 422 that is coupled to the inner sleeve of the cutter. The rotor 422 may have two adjacent N magnetized poles and two adjacent S magnetized poles. The motor 404 may have a stop magnet 423 which is magnetized to attract the N poles and repel the S poles. Thus when the motor 404 is stopped the stop magnet 423 will always orient the rotor 422 in the position shown in FIG. 22a. The attached inner sleeve of the cutter will therefore always stop in the same position. By way of example, the inner sleeve may always stop in an open port position. The motor 404 may have an additional stop magnet 424 that is magnetized to attract the S poles of the rotor 422.

The conventional Hall Effect sensors that are typically located in a quadrant of the motor may be removed. An external two pole magnet (not shown) may be connected to the rotor and coupled to the sensor 416. The sensor may be a single Hall Effect sensor. The two pole magnet rotates with the motor rotor relative to the Hall Effect sensor 416.

FIG. 23 shows a digital feedback signal of the motor sensor 416. The sensor 416 provides a "high" output signal when the motor 404 is in the first 180° of rotation and a "low" output when the motor rotates through the next 180°. The controller 410 utilizes the feedback signal to determine the position of the motor 404 and the timing of the commutation signals.

When the motor 404 is stopped the controller 410 may enter a routine to initially determine the motor position from the feedback signal. If the motor 404 is not in the desired start/stop position the controller 410 can provide the appropriate output signals to move the motor 404 into the desired start/stop position.

The controller 410 can also provide load compensation for the motor 404. The controller 410 can compare a desired motor movement with the actual movement of the motor 404 from the feedback signal of the sensor 416, and then vary the output signals of the driver 418 to compensate for any discrepancy between the desired and actual values. For example, the controller 404 can provide signals to adjust the current to the motor by comprising a lead or lag between the feedback signal from the sensor 416 with a desired value. Referring to FIG. 22, the controller 410 may change the frequency and/or width(s) of the pulses to vary the amount of energy provided to the motor 404 to compensate for varying motor loads.

Referring to FIG. 21, the inner sleeve 406 of the handpiece can be coupled to a vacuum source 425 and a vacuum reservoir 426 by a vacuum line 427. The pressure of the vacuum line 426 and reservoir 425 are controlled by a variable regulator valve 428. The valve 428 may be a device sold by Coast Pneumatics of Fullerton, Calif. under the product designation V-800.

The valve 428 has an electronic interface 430 that is coupled to the controller 410. The controller 410 provides output signals to the interface 430 to control the position of the valve 428 and the pressure within the vacuum line 427.

The system may further have a pressure transducer 432 that is coupled to the controller 410. The pressure transducer 432 provides a feedback signal that corresponds to the actual pressure within the vacuum line 427. The controller 410 may have a closed loop feedback routine to vary the output signals to the regulator valve 428 to insure that the vacuum pressure is maintained at a desired level or within a desired bandwidth.

The controller 410 may operate to control the effective size of the port 409 and the cutting action of the device. The controller 410 can vary the effective port opening by changing the commutation signals so that the motor 404 does not rotate 360° and the inner sleeve 406 does not move to the full distal position. By way of example, the controller 410 can drive the motor 404 to rotate 90° in a clockwise direction and then drive the motor 90° in a counterclockwise direction so that the inner sleeve 406 moves one-half of the full sleeve stroke.

The foot pedal 412 may have a switch(es) 434 which allows the system to operate in one of two modes. In one mode, referred to as a variable speed mode, the controller 410 varies the speed of the motor 404 through the operator input of the pedal 412. When the variable speed mode is selected the operator can vary the speed of the motor by depressing the pedal 412. The vacuum pressure is typically held at a constant level in this mode.

In another mode, referred to as a variable pressure mode, the controller 410 varies the vacuum pressure of the system through the valve 428 in response to input through the foot pedal 412. In this mode, the operator is allowed to vary the vacuum pressure of the system through the pedal 412. The speed of the motor 404 is typically held at a constant level in this mode.

The system may further have an exhaust valve 436 that is connected to the vacuum line 424. The exhaust valve 436 can be opened to rapidly return the system to atmospheric pressure. The software routine may be such that the exhaust valve 436 is opened and the motor 404 is no longer driven when the controller 410 determines that the motor 404 is no longer moving the inner sleeve 406. Such a mode of operation prevents vacuum pressure within line 426 from pulling tissue into the device if the motor 404 malfunctions or some other event prevents the inner sleeve 406 from the moving.

FIGS. 24 and 25 show an alternate embodiment of a slider 450 that is attached to an inner sleeve 452. The slider 450 has a groove 454 that receives a wobble plate (not shown) of a handpiece. The wobble plate can be the same or similar to the component shown in FIG. 1. The slider 450 has a pair of flat keying surfaces 456 that cooperate with corresponding surfaces of the handpiece to insure that the inner sleeve 454 is assembled in a correct orientation. To insure that the slider 454 can be readily attached to the wobble plate the controller 410 moves the motor 404 to a start position when the motor 404 is turned off so that the wobble plate is aligned with the groove 454.

FIG. 26 shows an alternate embodiment of a system which has a console 460 that contains the motor 404 and the electronics to operate the system. The motor 404 is coupled to a wobble plate or other inner sleeve drive mechanism within a handpiece 462 by a cable 464. The motor 404 rotates the cable 462. The cable 462 actuates the drive mechanism and induces a cutting action of the surgical device. The cable 464 may be located within a protective sheath 466. Placing the motor 404 within the console 460 may reduce the size and vibration of the handpiece 462.

Figure 27:
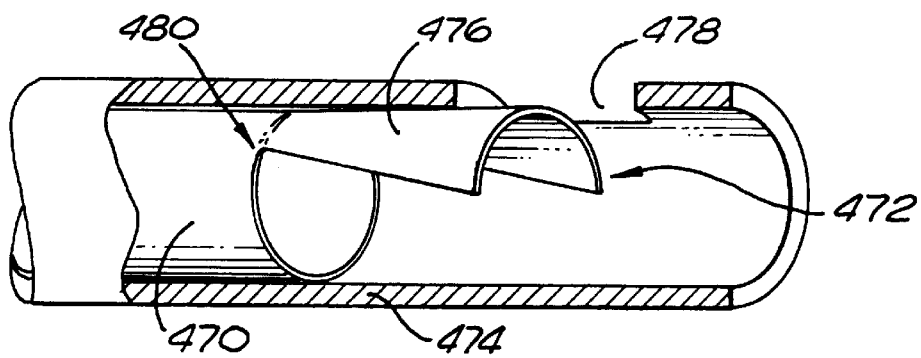
FIG. 27 is a perspective view of an inner sleeve of the cutter.

FIG. 27 shows an alternate embodiment of an inner sleeve 470 which has a tip 472 that exerts a spring force on an outer sleeve 474. The inner sleeve 470 has a lip 476 located adjacent to an aspiration port 478 of the outer sleeve 474.

The lip 476 is bent at the base 480 so that the tip 472 is slightly deflected in a direction toward the outer sleeve 474. The bend and amount of spring deflection can be varied for different inner sleeves. Different tissues may be severed more effectively with different spring forces. With the present invention, a surgeon may assemble an inner sleeve 470 which has a spring force that is optimal for a particular tissue.

Figure 28:
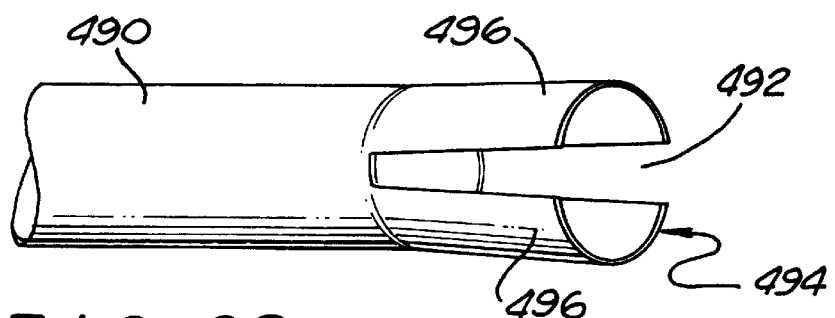
FIG. 28 is a perspective view of an alternate embodiment of the inner sleeve.

FIG. 28 shows another inner sleeve 490 which has a pair of longitudinal slits 492 in the tip 494 to create two lips 496. The lips 496 are bent in an outward radial direction to create a spring deflection of the tip 494. The length and/or width of the slits 492 can be varied to change the spring force of the tip 494.

Figure 29:
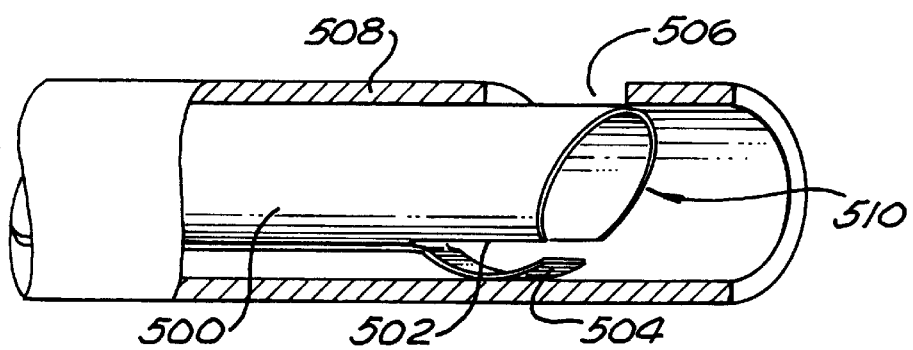
FIG. 29 is a perspective view of an alternate embodiment of the inner sleeve.

FIG. 29 shows an alternate embodiment of an inner sleeve 500 which has two longitudinal slits 502 which create a spring lip 504. The spring lip 504 is typically located opposite an aspiration port 506 of an outer sleeve 508. The lip 504 exerts a spring force that pushes the tip 510 of sleeve 500 toward the outer sleeve 508. The spring force of the lip 504 can be varied for different inner sleeves 500.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical device, comprising:
   a handpiece;
   a motor that is attached to said handpiece;
   a wobble plate that is connected to said motor;
   a slider that is coupled to said wobble plate, said slider having a key surface that aligns said slider with said handpiece;
   an outer sleeve that is coupled to said handpiece;
   an inner sleeve that is attached to said slider and can move relative to said outer sleeve.

2. The system as recited in claim 1, further comprising a controller that aligns said wobble plate with said groove of said slider when said motor is in a start condition.

3. A surgical device, comprising:
   an outer sleeve that has an aspiration port which is in fluid communication with an inner channel of said outer sleeve;
   an inner sleeve that is located within said inner channel, said inner sleeve having a tip that has a circumferential slit and a preexisting bend before insertion into said inner sleeve so that said tip exerts a spring force on said outer sleeve; and,
   a motor that moves said inner sleeve relative to said outer sleeve.

4. The device as recited in claim 3, wherein said inner sleeve has a pair of slits.

* * * * *

UNITED STATES PATENT AND TRADEMARK OFFICE
CERTIFICATE OF CORRECTION

PATENT NO.    : 6,258,111 B1
DATED         : July 10, 2001
INVENTOR(S)   : Rod Ross It is certified that error appears in the above-identified patent and that said Letters Patent is hereby corrected as shown below:

Column 14,
Line 49, please insert after "channel" -- of said outer sleeve --.
Line 52, please change "inner sleeve" to -- outer sleeve --.

Signed and Sealed this

Twenty-fourth Day of December, 2002

JAMES E. ROGAN
*Director of the United States Patent and Trademark Office*